United States Patent
Pan et al.

(10) Patent No.: US 11,786,365 B2
(45) Date of Patent: Oct. 17, 2023

(54) PROSTHETIC TISSUE VALVE AND METHOD OF TREATING THE SAME

(71) Applicant: Peijia Medical (Suzhou) Co., Ltd., Suzhou (CN)

(72) Inventors: Kongrong Karl Pan, Suzhou (CN); Yi Zhang, Suzhou (CN); Kun Zhang, Suzhou (CN); Yongjian Wu, Suzhou (CN); Mao Chen, Suzhou (CN); Yida Tang, Suzhou (CN)

(73) Assignee: PEIJIA MEDICAL (SUZHOU) CO., LTD., Suzhou (CN)

( * ) Notice: Subject to any disclaimer, the term of this patent is extended or adjusted under 35 U.S.C. 154(b) by 481 days.

(21) Appl. No.: 16/840,289

(22) Filed: Apr. 3, 2020

(65) Prior Publication Data

US 2021/0220125 A1 Jul. 22, 2021

(30) Foreign Application Priority Data

Jan. 22, 2020 (CN) .......................... 202010074284.4

(51) Int. Cl.
*A61F 2/24* (2006.01)
*B29C 71/00* (2006.01)
(Continued)

(52) U.S. Cl.
CPC .......... *A61F 2/2415* (2013.01); *A01N 1/0284* (2013.01); *A61L 27/34* (2013.01);
(Continued)

(58) Field of Classification Search
CPC ...... A61F 2/2415; A01N 1/0284; A61L 27/34
(Continued)

(56) References Cited

U.S. PATENT DOCUMENTS 5,336,616 A 8/1994 Livesey et al.
10,052,201 B2 * 8/2018 Zhang ................... A61F 2/2418
(Continued)

FOREIGN PATENT DOCUMENTS

CN 109549761 A 4/2019
CN 110193095 A 9/2019
(Continued)

OTHER PUBLICATIONS

Chinese Second office action, Chinese Application No. 202010074284.4 dated Dec. 3, 2021(29 pages).
(Continued)

*Primary Examiner* — Stephen M Gravini

(57) ABSTRACT

A prosthetic tissue valve and a method of treating the prosthetic tissue valve are provided. The method includes: decreasing a temperature of a chamber carrying the prosthetic tissue valve from a first preset temperature to a second preset temperature in a first cooling rate; decreasing the temperature of the chamber carrying the prosthetic tissue valve from the second preset temperature to a third preset temperature in a second cooling rate; and performing a drying process to the prosthetic tissue valve. The second preset temperature is a critical crystallization temperature and is greater than a crystallization temperature of the prosthetic tissue valve. The third preset temperature is lower than the crystallization temperature of the prosthetic tissue valve, and the second cooling rate is greater than the first cooling rate.

12 Claims, 3 Drawing Sheets

(51) Int. Cl.

| | |
|---|---|
| *A61L 27/36* | (2006.01) |
| *A61L 27/54* | (2006.01) |
| *A61L 27/34* | (2006.01) |
| *A61L 33/00* | (2006.01) |
| *A61L 33/08* | (2006.01) |
| *A01N 1/02* | (2006.01) |
| *B29K 71/00* | (2006.01) |
| *B29L 31/00* | (2006.01) |

(52) U.S. Cl.
CPC ....... *A61L 27/3687* (2013.01); *A61L 27/3691* (2013.01); *A61L 27/54* (2013.01); *A61L 33/0011* (2013.01); *A61L 33/08* (2013.01); *B29C 71/0009* (2013.01); *B29C 71/0063* (2013.01); *A61F 2240/001* (2013.01); *A61F 2250/0067* (2013.01); *A61L 2300/236* (2013.01); *A61L 2300/414* (2013.01); *A61L 2300/42* (2013.01); *A61L 2300/606* (2013.01); *A61L 2300/802* (2013.01); *A61L 2400/02* (2013.01); *A61L 2420/02* (2013.01); *A61L 2420/06* (2013.01); *B29K 2071/02* (2013.01); *B29L 2031/7534* (2013.01)

(58) Field of Classification Search
USPC .......................................................... 34/287
See application file for complete search history.

(56) References Cited

U.S. PATENT DOCUMENTS

| 10,589,003 | B2 * | 3/2020 | Raad ....................... A01N 25/24 |
| 11,364,115 | B2 * | 6/2022 | Wang ..................... A61F 2/2409 |
| 2004/0105999 | A1 * | 6/2004 | Abkowitz ............... B32B 15/01 |
| | | | 428/629 |
| 2006/0241754 | A1 * | 10/2006 | Beisang .................... A61F 2/12 |
| | | | 623/8 |
| 2007/0141107 | A1 * | 6/2007 | Kutryk .................... A61L 31/16 |
| | | | 623/1.42 |
| 2012/0172979 | A1 * | 7/2012 | DuMontelle .......... A61F 2/2412 |
| | | | 623/2.12 |
| 2018/0104282 | A1 | 4/2018 | Sinclair et al. |
| 2019/0117841 | A1 | 4/2019 | Ashworth |
| 2019/0154336 | A1 * | 5/2019 | Weisbeck ............... A61C 13/20 |
| 2021/0220125 | A1 * | 7/2021 | Pan ....................... A01N 1/0289 |

FOREIGN PATENT DOCUMENTS

| EP | 0564786 A2 | 10/1993 | |
| EP | 3298987 A1 * | 3/2018 | .......... A61F 2/2412 |
| JP | 7036556 B2 * | 3/2022 | .......... A61F 2/2412 |
| WO | WO-2018057257 A1 * | 3/2018 | .......... A61F 2/2412 |

OTHER PUBLICATIONS

The extended European search report for Application No. 20166883. 7-1109 dated Jun. 11, 2021.(7 pages).
Camila F Borgognoni,The Influence of Freezing Rates on Bovine Pericardium Tissue Freeze-Drying,Brazilian Arch. Biol. Technol., Jan. 1, 2009, p. 1493-1504, XP055754814.
Sabra Zouhair et al,Preservation strategies for decellularized pericardial scaffolds for off-the-shelf availability, Acta Biomaterialia, vol. 84, Jan. 1, 2019, p. 208-221,XP055754807.
Chinese First office action, Chinese Application No. 202010074284.4 dated Sep. 16, 2021(17 pages).
European Examination report,European Application No. 20166883. 7, dated Mar. 10, 2023 (6 pages).

* cited by examiner

PROSTHETIC TISSUE VALVE AND METHOD OF TREATING THE SAME

CROSS REFERENCE TO RELATED APPLICATIONS

The present application claims priority of China Patent Application No. 202010074284.4, filed on Jan. 22, 2020, in China National Intellectual Property Administration, the contents of which are herein incorporated by reference in its entirety.

TECHNICAL FIELD

The present disclosure relates to the field of medical technologies, and in particular to a prosthetic tissue valve and a method of treating a prosthetic tissue valve.

BACKGROUND

Diseases related to heart valves endanger human health and lives, and significantly impacts quality of patients' daily working and life. Conventional therapeutic strategies include conservative treatments with medicines and surgical replacement of heart valves. Although surgeries significantly improve prognosis, elder patients are usually suffering from multiple complicated diseases, such as cardiopulmonary dysfunction, and therefore, may not be tolerant to thoracotomy surgeries. Compared with surgeries, transcatheter intervention of a prosthetic tissue valve for treatments is minimally invasive, leaves a short period of time for recovery, and does not generate scars, which is beneficial to many patients.

Being limited by treatments of prosthetic tissue valves in the related art, a prosthetic tissue valve used in a system of the transcatheter intervention of a prosthetic tissue valve is required to be stored in a preservation solution (such as glutaraldehyde solution). After the prosthetic tissue valve being removed out of the preservation solution, functions of the prosthetic tissue valve may be reduced in a short period of time. Long distance transportation of the prosthetic tissue valve in the preservation solution may not be convenient. In addition, the prosthetic tissue valve is required to be washed repeatedly before a surgery to remove majority of the preservation solution remaining on the prosthetic tissue valve, and a manufacturer is required to assign professionals to assemble the prosthetic tissue valve with a delivery device before the surgery. Therefore, time consumed to prepare the surgery may be long, improving costs for the surgery. At the same time, the prosthetic tissue valve available in the market may have some intrinsic defects. For example, an average of a long term service life for the prosthetic tissue valve may be 10 to 15 years. A main reason of dysfunction of the prosthetic tissue valve may be calcification of the tissue valve. In a recent clinical study, an incidence rate of thrombus formation caused by the prosthetic tissue valve is relatively high. Therefore, a patient may need to receive an extra anticoagulant treatment and have medical check-up regularly after the surgery. If treatments are not performed promptly, dysfunction of the prosthetic tissue valve at an early stage may occur, reducing the service life of the prosthetic tissue valve.

Therefore, there may be a large clinical demand of a prosthetic tissue valve able to be anticoagulant, antithrombotic, anti-calcification, having better functions, safe, long-period preserved in a dehydrated condition, and instantly used.

In the related art, some treatments to a biological tissue or a prosthetic tissue valve to allow the tissue or valve to be preserved in a dry state may have some problems to be solved.

1. According to a lyophilization method in the art, a freezing process and a drying process are included, the freezing process may not be uniformly performed to each area of the biological tissue or the prosthetic tissue valve to be treated. In such a way, a thermal stress may be generated from an inside of the prosthetic tissue valve during the freezing process, damaging the biological tissue.

2. During performing the freezing process to the entire biological tissue or the prosthetic tissue valve to be treated, a crystallization rate of each area may be different, such that a crystal size of each area may be different. In one aspect, a large sized crystal may damage an internal structure of the biological tissue. In another aspect, a sublimation rate of each area during the drying process may be different, and a drying degree of each area may be different. An area that is dried insufficiently may contain more residual water, and may be difficult to be preserved, whereas biological functions of an area that is dried excessively may be reduced.

3. According to the lyophilization method in the art, an appropriate strategy for regulating a sublimation dyring process may be unavailable. Typically, the biological tissue may be rewarmed to an ambient temperature after being dried for a certain period of time. In one aspect, during rewarming from a low temperature, the residual water may not be controlled, causing damages to the biological tissue. In another aspect, after the drying process is completed, residual water may be excessive (for example, according to some methods in the art, the residual water may be 15% to 30%). As water may be a major substance involved in biochemical reactions, a large amount of water may impact long-term preservation of the prosthetic tissue valve.

4. According to the lyophilization method in the art, to improve a glass transition temperature to allow the biological tissue to be maintained in a glassy state within a range of −40° C. to 0° C., a high concentration of a lyoprotectant may be used. The high concentration of the lyoprotectant may have high toxicity, damaging the biological tissue. In a subsequent drying process, the high concentration of the lyprotectant may not be removed and may remain on the biological tissue, reducing biocompatibility of the biological tissue.

In addition, post-surgery thrombosis of an interventional valve needs to be treated by an oral anticoagulant therapy, and an appropriate commercial product to solve the post-surgery thrombosis is not available in the market.

SUMMARY OF THE DISCLOSURE

The present disclosure may provide a prosthetic tissue valve and a method of treating the prosthetic tissue valve, and the method may provide a prosthetic tissue valve able to be preserved in a dry state.

According to a first aspect of the present disclosure, a method of treating a prosthetic tissue valve is provided. The method includes: decreasing a temperature of a chamber carrying the prosthetic tissue valve from a first preset temperature to a second preset temperature in a first cooling rate; decreasing the temperature of the chamber carrying the prosthetic tissue valve from the second preset temperature to a third preset temperature in a second cooling rate; and performing a drying process to the prosthetic tissue valve. The second preset temperature is greater than a crystallization temperature of the prosthetic tissue valve, and the second preset temperature is a critical crystallization temperature. The third preset temperature is lower than the crystallization temperature of the prosthetic tissue valve, and the second cooling rate is greater than the first cooling rate.

According to a second aspect of the present disclosure, a prosthetic tissue valve is provided. The prosthetic tissue valve is obtained by performing the method as described in the first aspect.

BRIEF DESCRIPTION OF THE DRAWINGS

In order to illustrate technical solutions of embodiments of the present disclosure in details, drawings required for illustrating the embodiments will be described in brief. Obviously, the following drawings illustrate only some embodiments of the present disclosure, and to any one of skill in the related art, other drawings may be obtained based on the following drawings without any creative work.

DETAILED DESCRIPTION

Figure 1:
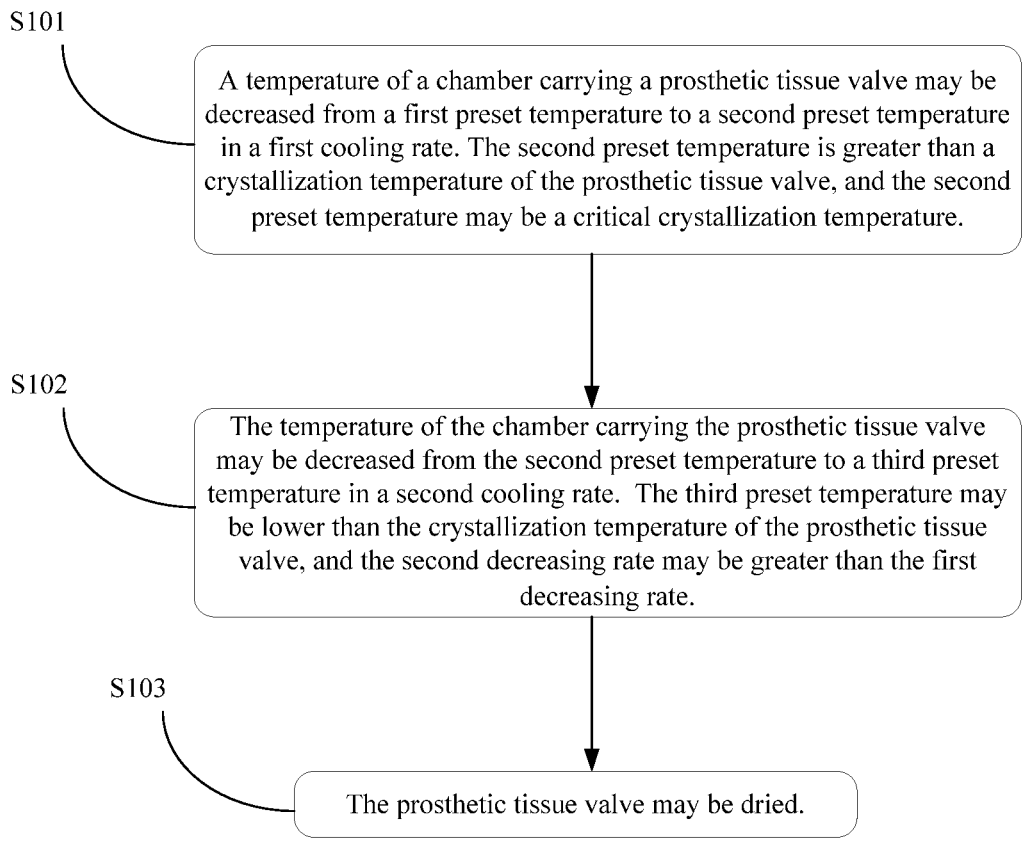
FIG. 1 is a flow chart of a method of treating a prosthetic tissue valve according to an embodiment of the present disclosure.

Technical solutions of the embodiments of the present disclosure may be described clearly and comprehensively by referring to the drawings. Obviously, illustrated embodiments are only a part of, but not all of, the embodiments of the present disclosure. Based on the embodiments of the present disclosure, any other embodiments obtained by any one of skill in the art without performing creative work should be within the scope of the present disclosure.

As shown in FIG. 1, a flow chart of a method of treating a prosthetic tissue valve is provided. The method may include following operations.

In an operation of S101, a temperature of a chamber carrying a prosthetic tissue valve may be decreased from a first preset temperature to a second preset temperature in a first cooling rate. The second preset temperature is higher than a crystallization temperature of the prosthetic tissue valve, and the second preset temperature may be a critical crystallization temperature.

Specifically, in the present embodiment, the prosthetic tissue valve may be an aortic valve, a mitral valve, a tricuspid valve, and a pulmonary valve, which are obtained by extracting from animal tissues. Alternatively, the prosthetic tissue valve may be an animal tissue, such as bovine pericardium, porcine pericardium, and the like. The chamber carrying the prosthetic tissue valve may be a heat insulation chamber with multiple channels and a degree of sealing of the chamber may be adjusted.

In addition, prosthetic tissue valves receiving different pre-treatments may have different crystallization temperatures. For example, the crystallization temperature may be within a range of −50° C. to 0° C. The first preset temperature in the operation of S101 may be within a range of 0° C. to 10° C. (such as 4° C., 6° C., 8° C., or the like). A difference between the second preset temperature (i.e., the critical crystallization temperature) and the crystallization temperature of the prosthetic tissue valve may be greater than 0° C. and smaller than or equal to 10° C. (such as 4° C., 6° C., 8° C., and the like). The first decreasing rate may be within a range of 0.1° C./min to 10° C./min (such as, 1° C./min, 5° C./min, and the like).

In one embodiment, the operation of S101 may specifically include: reducing the temperature of the chamber carrying the prosthetic tissue valve from 4° C. to −15° C. in 1° C./min, such that each area of the prosthetic tissue valve may have same temperature and may be in the critical crystallization state.

In an operation of S102, the temperature of the chamber carrying the prosthetic tissue valve may be decreased from the second preset temperature to a third preset temperature in a second cooling rate. The third preset temperature may be lower than the crystallization temperature of the prosthetic tissue valve, and the second cooling rate may be greater than the first cooling rate.

Specifically, in the present embodiment, the second cooling rate may within a range of 10° C./min to 100° C./min (such as 20° C./min, 50° C./min, 80° C./min, 99° C./min, and the like). A ratio of the second cooling rate to the first cooling rate may be set to be as large as possible, such as greater than 10 or the like. The third preset temperature may be within a range of −200° C. to −5° C. (such as, −70° C., −120° C., −180° C., and the like).

In one embodiment, the operation of S102 may specifically include: decreasing the temperature of the chamber carrying the prosthetic tissue valve from −15° C. to −70° C. in 99° C./min. The temperature may be rapidly decreased from the critical crystallization temperature to a temperature lower than the critical crystallization, such that each area of the prosthetic tissue valve may be crystallized rapidly at the same time, ensuring each area of the prosthetic tissue valve to have a same temperature during crystallization and avoiding a damage to the prosthetic tissue valve caused by a thermal stress generated due to a temperature difference. At the same time, the prosthetic tissue valve may have uniformly sized crystals, such that in a subsequent drying process, each area of the prosthetic tissue valve may have a same drying degree. In addition, a relatively high second cooling rate is applied, and sizes of the crystals are relatively small, avoiding a damage to the prosthetic tissue valve caused by a large sized crystal.

In an operation of S103, the prosthetic tissue valve may be dried.

Specifically, vacuum freeze-drying may be performed to the prosthetic tissue valve. For example, a pressure of vacuum may be set to be within a range of 100 Pa to 5 Pa (such as, 20 Pa, 50 Pa, 70 Pa, and the like) to completely remove free water.

According to an implementation, the prosthetic tissue valve may be cooled by: uniformly spraying liquid nitrogen into a mist form into the chamber carrying the prosthetic tissue valve to generate a temperature field containing scattered mist-formed liquid nitrogen surrounding the prosthetic tissue valve. A concentration of the mist-formed liquid nitrogen (such as a volume fraction or the like) may be positively correlated with an internal temperature of the chamber and the cooling rate. For example, the higher the concentration of the liquid nitrogen, the higher the cooling rate of the chamber, and the lower the internal temperature of the chamber may reach. The above-mentioned treatment may be performed easily, and the mist-formed liquid nitrogen serving as a medium for cooling may have high thermal conductivity. Each area of the prosthetic tissue valve having a complex three-dimensional structure may be fully exposed to the mist-formed liquid nitrogen, such that the cooling rate and an instant temperature during cooling of each area may be uniform.

Figure 2:
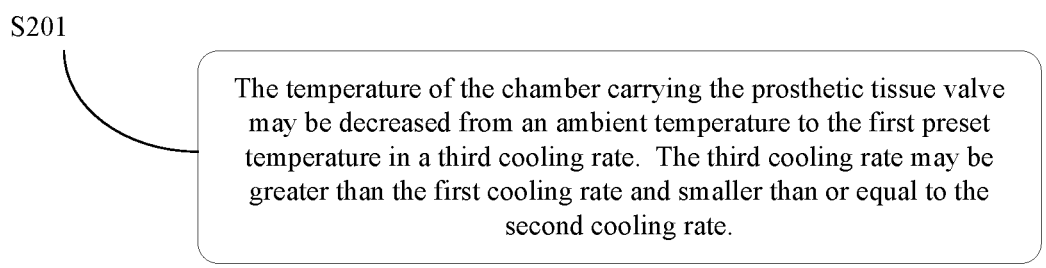
FIG. 2 is a flow chart of a method of treating a prosthetic tissue valve performed before an operation of S101 shown in FIG. 1.

In another implementation, as shown in FIG. 2, a flow chart of a method of treating a prosthetic tissue valve performed before an operation of S101 shown in FIG. 1 is provided. Before performing the operation of S101, the treatment provided in the present disclosure may further include following operations.

In an operation of S201, the temperature of the chamber carrying the prosthetic tissue valve may be decreased from an ambient temperature to the first preset temperature in a third cooling rate. The third cooling rate may be greater than the first cooling rate and smaller than or equal to the second cooling rate.

Specifically, an initial temperature of an inside of the chamber may be equal to the ambient temperature, such as 25° C. or the like. To reduce time consumed for treating the prosthetic tissue valve, a medium or high cooling rate may be applied to reduce the temperature of the inside of the chamber carrying the prosthetic tissue valve to the first preset temperature. In the present embodiment, the third cooling rate may be within a range of 10° C./min to 100° C./min (such as, 20° C./min, 50° C./min, 70° C./min, and the like).

In other embodiments, without considering the time consumed for treating the prosthetic tissue valve, the above-mentioned operation of S201 may be omitted, and the first preset temperature in the operation of S101 may be the ambient temperature. The operation of S101 may be decreasing the temperature of the chamber carrying the prosthetic tissue valve from the ambient temperature to the second preset temperature in the first cooling rate, and the second preset temperature may be greater than or equal to the crystallization temperature of the prosthetic tissue valve.

In one embodiment, the operation of S201 may specifically include: decreasing the temperature of the chamber carrying the prosthetic tissue valve from the ambient temperature to 4° C. in 20° C./min.

Figure 3:
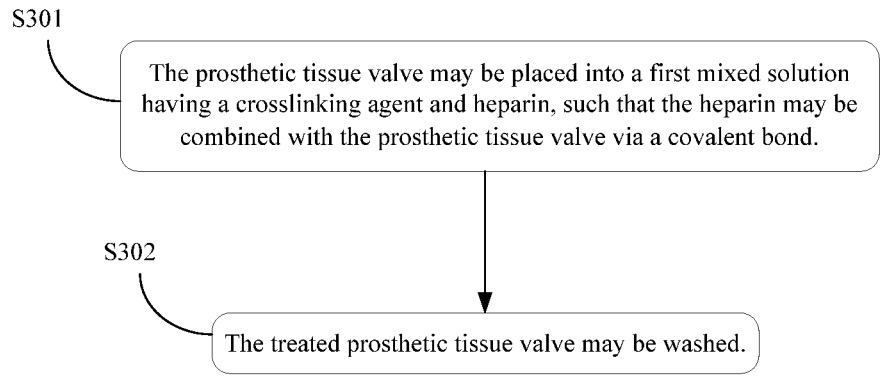
FIG. 3 is a flow chart of a method of treating a prosthetic tissue valve performed before an operation of S201 shown in FIG. 2.

Further, as shown in FIG. 3, a flow chart of a method of treating a prosthetic tissue valve performed before an operation of S201 shown in FIG. 2 is provided. Before performing the operation of S201, the treatment provided in the present disclosure may further include following operations.

In an operation of S301, the prosthetic tissue valve may be placed and incubated into a first mixed solution having a crosslinking agent and heparin, such that the heparin may bind to the prosthetic tissue valve via a covalent bond.

Specifically, before performing the operation of S301, the treatment provided by the present disclosure may include performing a crosslinking treatment (such as glutaraldehyde crosslinking or photo-oxidation crosslinking) to a raw membrane (such as bovine pericardium, porcine pericardium) of the prosthetic tissue valve; and washing the prosthetic tissue valve with normal saline. In such a way, a crosslinking degree and a relative molecular weight of type I collagen of the raw membrane may be improved, such that chemical stability, an enzyme-resistant property, and mechanical stability of a crosslinked prosthetic tissue valve may be improved.

In the present embodiment, the crosslinking agent in the operation of S301 may include N-hydroxy succinimide (NHS) and 1-(3-Dimethylaminopropyl)-3-ethylcarbodiimide hydrochloride (EDC). EDC and NHS may enable the heparin to covalently bind with the prosthetic tissue valve and further enable the prosthetic tissue valve to have a secondary crosslinking to improve the degree of crosslinking, the enzyme-resistant property, and the mechanical stability.

A concentration of the heparin in the first mixed solution may be 1 to 40 g/L (such as 10 g/L, 20 g/L, 30 g/L, or the like), a concentration of NHS in the first mixed solution may be 1-10 g/L (such as 2 g/L, 5 g/L, 8 g/L, or the like), EDC in the first mixed solution may be 1-50 g/L (such as 10 g/L, 20 g/L, 30 g/L, or the like). In one embodiment, the first mixed solution may include 3 g/L of heparin, 4 g/L of EDC, and 2.4 g/L of NHS.

In one embodiment, the operation of S301 may specifically include: placing the prosthetic tissue valve into the first mixed solution having EDC, NHS, and heparin, and incubating the prosthetic tissue valve at 30° C. to 50° C. (such as 37° C. or the like) for 1 hour to 8 hours (such as 4 hours or the like).

According to the operation of S301, the heparin may be covalently binding to the prosthetic tissue valve, such that after being implanted into a patient, the prosthetic tissue valve may show the anticoagulation function and inhibit platelets from gathering, and post-surgery anticoagulation treatment and an incidence rate of post-surgery thrombus formation may be reduced.

In addition, in other embodiments, the first mixed solution may further include growth factors, including a vascular endothelial growth factor (VEGF). A concentration of VEGF in the first mixed solution may be 1 ng/mL to 100 ng/mL (such as 10 ng/mL, 50 ng/mL, 80 ng/mL, and the like). By performing the above-mentioned treatment, the VEGF may be covalently binding to the prosthetic tissue valve. After being implanted into the patient, the prosthetic tissue valve may be induced by VEGF to be endothelialized. Endothelial cells growing on a surface of the prosthetic tissue valve may reduce post-surgery thrombus formation and reduce enrichment of calcium to prevent calcification of the prosthetic tissue valve.

In an operation of S302, the treated prosthetic tissue valve may be washed.

Specifically, in one embodiment, the operation of S302 may include: placing the prosthetic tissue valve, which is treated by the operation of S301, into a solution of disodium hydrogen phosphate for washing for 2 hours, and then placing the prosthetic tissue valve into water for injection (i.e., ultrapure water) for washing for 24 hours to remove heparin and crosslinking agent remaining on, but unbinding to, the surface of the prosthetic tissue valve.

In other embodiments, before performing the operation of S201, for example, before the operation of S301 or after performing the operation of S302, the treatment provided by the present disclosure may further include: placing the prosthetic tissue valve into a second mixed solution. The second mixed solution may include a lyoprotectant, an antioxidant, and growth factors. As another example, the second mixed solution may include the lyoprotectant and the antioxidant. As still another example, the second mixed solution may include the lyoprotectant and the growth factors.

Specifically, the lyoprotectant may include at least one of glycerin, trehalose, sucrose, polyvinylpyrrolidone, glycol, propylene glycol, acetamide, methanol, polyethylene glycol, and glucan. The above-mentioned lyoprotectant may protect the prosthetic tissue valve from being damaged during a subsequent lyophilization process. The antioxidant may include at least one of vitamin D, vitamin E, protein hydrolysates, sodium thiosulfate, and thiourea. The above-mentioned antioxidant may protect the lyophilized prosthetic tissue valve from being oxidized when contacting oxygens, improving preservation time of the prosthetic tissue valve. The growth factors may include the VEGF, and the VEGF may covalently bind to the prosthetic tissue valve. After implanting the prosthetic tissue valve, the VEGF may induce the surface of the prosthetic tissue valve to be endolialized, and the endothelial cells growing on the surface of the prosthetic tissue valve may reduce post-surgery thrombus formation and reduce enrichment of calcium, preventing calcification of the prosthetic tissue valve.

A mass fraction of the above-mentioned lyoprotectant and antioxidant in the second mixed solution may not exceed 35% (such as 10%, 20%, 25%, and the like). The concentration of the growth factor in the second mixed solution may be 0 ng/mL to 100 ng/mL (such as, 10 ng/mL, 50 ng/mL, 80 ng/mL, and the like). In the present embodiment, a low concentration of lyoprotectant may be applied to reduce a damage to the prosthetic tissue valve brought by the lyoprotectant, harmful chemical reagents remaining on the prosthetic tissue valve may be reduced, and biocompatibility of the prosthetic tissue valve may be improved. The above-mentioned second mixed solution may include 10% (volume fraction) of glycerin, 5% (volume fraction) of vitamin E, 50 ng/mL of VEGF.

In an embodiment, the operation of placing the prosthetic tissue valve into the second mixed solution may include: placing the prosthetic tissue valve into the second mixed solution, incubating on a constant temperature shaker at 30° C. to 50° C., 100 rpm, for 1 hour to 24 hours (such as 22 hours or the like). A relatively high temperature and a relatively high shaking speed may be applied to increase an exposure area between the prosthetic tissue valve and lyoprotectant, the antioxidant, and the growth factors in the second mixed solution, such that the lyoprotectant, the antioxidant, and the growth factors may adequately and uniformly permeate into the prosthetic tissue valve, improving preservation effect of the treatment, such that a relatively high preservation effect may be achieved by using a relatively small amount of lyoprotectant.

In a situation of the first mixed solution and the second mixed solution both excluding the growth factor, before performing the operation of S201, the treatment provided by the present disclosure may include: placing the prosthetic tissue valve into a third mixed solution containing the growth factor. The growth factor may include the VEGF, and the concentration of VEGF in the third mixed solution may be 1 ng/mL to 100 ng/mL (such as 10 ng/mL, 50 ng/mL, 80 ng/mL, and the like). In other words, in the present disclosure, the growth factor may be added into the first mixed solution, the second mixed solution, or the third mixed solution.

Figure 4:
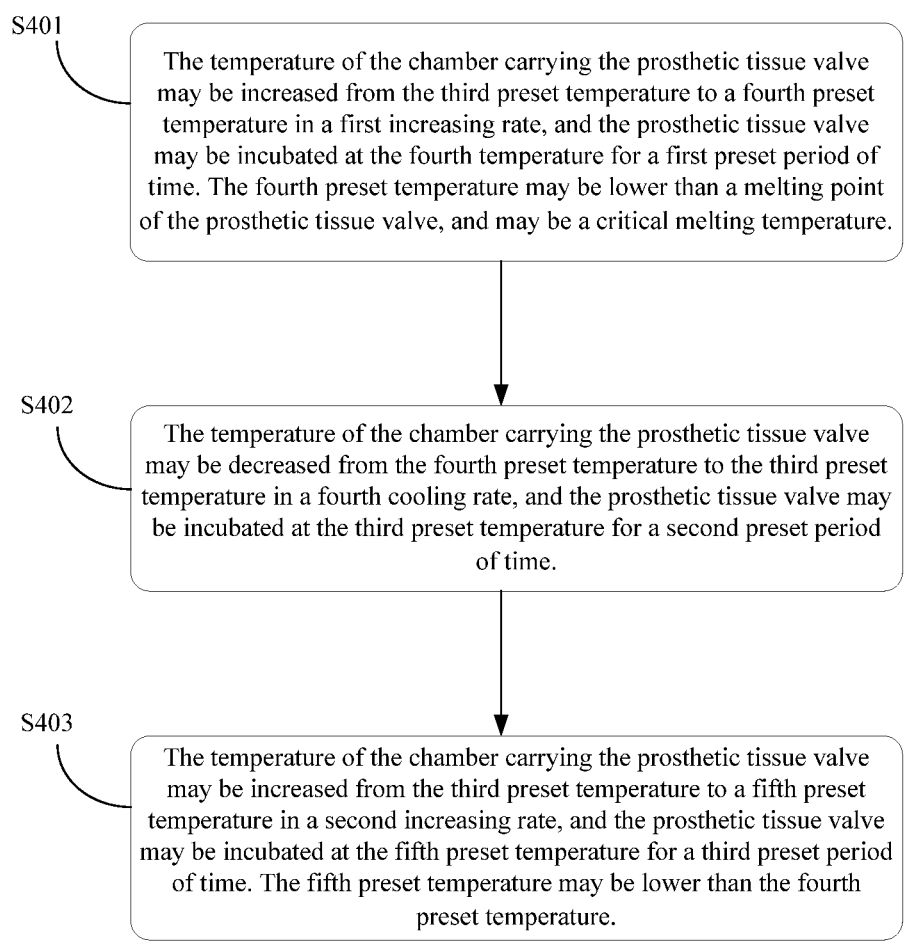
FIG. 4 is a flow chart of a method of treating a prosthetic tissue valve performed before an operation of S103 shown in FIG. 1.

In another implementation, as shown in FIG. 4, a flow chart of a method of treating a prosthetic tissue valve performed before an operation of S103 shown in FIG. 1 is provided. Between the operations of S102 and S103, the treatment provided by the present disclosure may further include following operations.

In an operation of S401, the temperature of the chamber carrying the prosthetic tissue valve may be increased from the third preset temperature to a fourth preset temperature in a first increasing rate, and the prosthetic tissue valve may be incubated at the fourth temperature for a first preset period of time. The fourth preset temperature may be lower than a melting point of the prosthetic tissue valve, and may be a critical melting temperature.

Specifically, the first increasing rate may be within a range of 0.1° C./min to 10° C./min (such as, 1° C./min, 5° C./min, 7° C./min, and the like). A temperature difference between the fourth preset temperature and the melting point may be greater than 0° C. and smaller than or equal to 10° C. The fourth preset temperature may be within a range of −50° C. to −5° C. (such as −15° C., −35° C., −45° C., and the like). The first preset period of time may be 1 hour to 3 hours (such as 2 hours and the like).

In one embodiment, the operation of S401 may include: increasing the temperature of the chamber carrying the prosthetic tissue valve from −70° C. to −15° C. in 1° C./min and incubating the prosthetic tissue valve at −15° C. for 1 hour.

In one operation of S402, the temperature of the chamber carrying the prosthetic tissue valve may be decreased from the fourth preset temperature to the third preset temperature in a fourth cooling rate, and the prosthetic tissue valve may be incubated at the third preset temperature for a second preset period of time.

Specifically, the fourth cooling rate may be within a range of 0.1° C./min to 10° C./min (such as, 1° C./min, 5° C./min, 7° C./min, and the like), and the second preset period of time may be 1 hour to 3 hours (such as 2 hours and the like).

In one embodiment, the operation of S402 may include: decreasing the temperature of the chamber carrying the prosthetic tissue valve from −15° C. to −70° C. in 1° C./min and incubating the prosthetic tissue valve at −70° C. for 1 hour.

In an operation of S403, the temperature of the chamber carrying the prosthetic tissue valve may be increased from the third preset temperature to a fifth preset temperature in a second increasing rate, and the prosthetic tissue valve may be incubated at the fifth preset temperature for a third preset period of time. The fifth preset temperature may be lower than the fourth preset temperature.

Specifically, the second increasing rate may be within the range of 0.1° C./min to 10° C./min (such as 1° C./min, 5° C./min, 7° C./min, and the like). The third preset period of time may be 1 hour to 3 hours (such as 2 hours and the like). The fifth preset temperature may be within a range of −100° C. to −40° C. (such as −80° C., −60° C., and the like).

In one embodiment, the operation of S403 may include: increasing the temperature of the chamber carrying the prosthetic tissue valve from −70° C. to −50° C. in 1° C./min, and incubating the prosthetic tissue valve at −50° C. for 1 hour.

During performing the operations of S401 to S403, the temperature of the chamber carrying the prosthetic tissue valve may be gradually increased to a temperature close to the critical melting temperature of the prosthetic tissue valve, gradually decreased, and then gradually increased. In such a way, crystals with different sizes may further be uniformized, such that in a subsequent drying process, each area of the prosthetic tissue valve may have a same drying degree.

Further, the operation of S103 in FIG. 1 may include: 1) performing a vacuum-drying process to the prosthetic tissue valve at the fifth preset temperature at a first vacuum degree for a fourth preset period of time; and 2) performing the vacuum-drying process to the prosthetic tissue valve at the fourth preset temperature at a second vacuum degree to completely remove free water in the prosthetic tissue valve. The first vacuum degree may indicate a pressure within a range of 10 Pa to 1 Pa (such as 8 Pa, 6 Pa, 4 Pa, and the like). The fourth preset period of time may be 1 hour to 10 hours (such as 2 hours, 4 hours, 6 hours, and the like). The second vacuum degree may be less than the first vacuum degree, and the second vacuum degree may indicate a pressure of 100 Pa to 5 Pa (such as, 80 Pa, 50 Pa, 20 Pa, and the like).

In one embodiment, the operation of S103 may include: lyophilizing the prosthetic tissue valve for 4 hours at $-50°$ C. at 1 Pa, and adjusting the pressure to be 50 Pa and increasing the temperature to $-15°$ C. to completely remove free water.

By applying a condition of freezing at a low temperature, all free water may be removed by sublimation, such that re-crystallization after rewarming may be avoided. Content of water within the prosthetic tissue valve may be reduced as much as possible, and structures and functions of the prosthetic tissue valve may be maintained. Further, during the above-mentioned drying process, remaining organic solvent may be removed firstly at the low temperature with a high vacuum degree, and free water may be removed by increasing the temperature and decreasing the vacuum degree, further reducing residual chemical reagents and improving biocompatibility of the prosthetic tissue valve.

In addition, to further remove the water within the prosthetic tissue valve to allow ≤15% of water eventually remained in the prosthetic tissue valve. After performing the above-mentioned operation to remove the free water, the treatment provided by the present disclosure further includes: increasing the temperature of the chamber carrying the prosthetic tissue valve from the fourth preset temperature to a sixth preset temperature in a third increasing rate; and performing the vacuum-drying process to the prosthetic tissue valve at the sixth preset temperature under a third vacuum degree. The second vacuum degree may be less than the third vacuum degree.

In the above-mentioned second drying process, the third increasing rate may be within a range of $0.1°$ C./min to $0.5°$ C./min (such as $0.2°$ C./min, $0.3°$ C./min, $0.4°$ C./min, and the like). The third vacuum degree may indicate a pressure of 30 Pa to 1 Pa (such as 5 Pa, 10 Pa, 20 Pa, and the like). The sixth preset temperature may be $20°$ C. to $30°$ C. (such as $25°$ C. and the like). The period of time for the drying process may be 1 hour to 5 hours (such as 2 hours, 3 hours, 4 hours, and the like).

In one embodiment, the above-mentioned second drying process may be: increasing the temperature of the chamber carrying the prosthetic tissue valve from $-15°$ C. to $20°$ C. in $0.5°$ C./min; and performing the vacuum-drying process to the prosthetic tissue valve at $20°$ C. at 1 Pa for 1 hour.

According to the above embodiment, the second drying process may be performed at an extremely high vacuum degree (i.e., an extremely low pressure) and a higher temperature, the efficiency of the second drying process may be improved, content of water, especially combined water, in the prosthetic tissue valve may be removed more quickly, such that the content of water in a final prosthetic tissue valve may be ≤15% (such as 5%, 10%, and the like). The preservation time of the prosthetic tissue valve may be significantly prolonged. In addition, by performing the drying process in separate stages, i.e., a first drying process and an intensive second drying process, remaining organic solvent may be removed as much as possible, further residual chemical reagents and improving biocompatibility.

Figure 5:
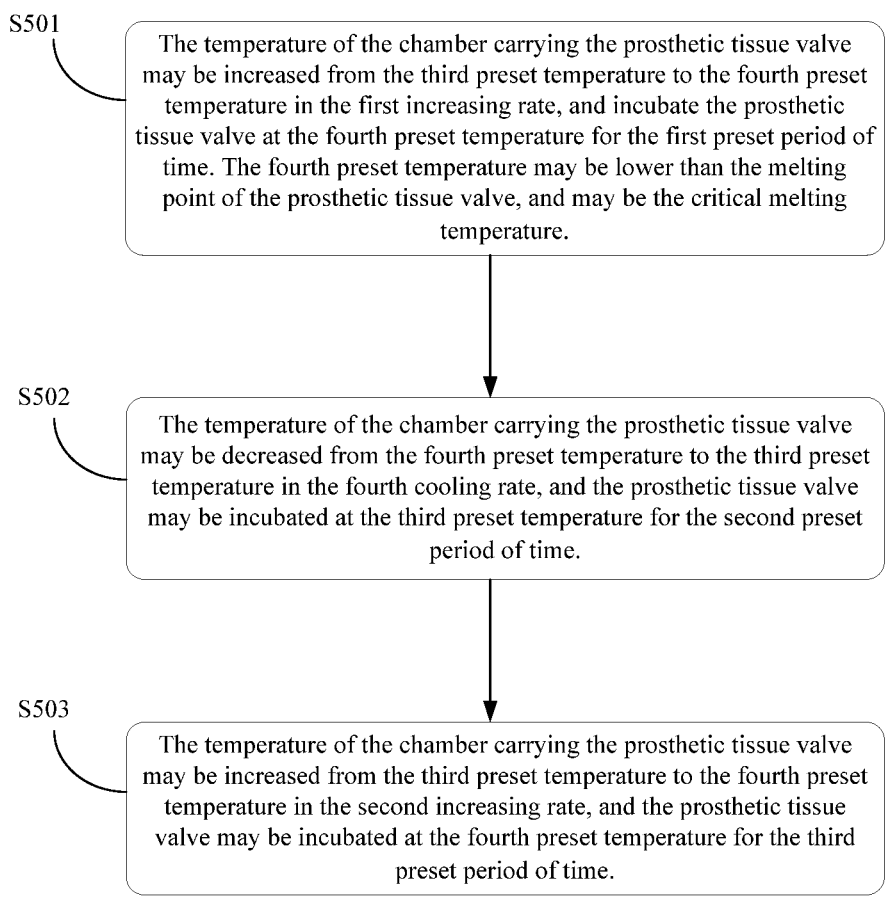
FIG. 5 is a flow chart of another method of treating a prosthetic tissue valve performed before an operation of S103 shown in FIG. 1

In another implementation, as shown in FIG. 5, a flow chart of another method of treating a prosthetic tissue valve performed before an operation of S103 shown in FIG. 1 is provided. Between performing the operations of S102 and S103, the treatment provided in the present disclosure may further include following operations.

In an operation of S501, the temperature of the chamber carrying the prosthetic tissue valve may be increased from the third preset temperature to the fourth preset temperature in the first increasing rate, and incubate the prosthetic tissue valve at the fourth preset temperature for the first preset period of time. The fourth preset temperature may be lower than the melting point of the prosthetic tissue valve, and may be the critical melting temperature.

Specifically, the operation may be the same as the operation of S401 shown in FIG. 4, and will not be repeatedly described herein.

In an operation of S502, the temperature of the chamber carrying the prosthetic tissue valve may be decreased from the fourth preset temperature to the third preset temperature in the fourth cooling rate, and the prosthetic tissue valve may be incubated at the third preset temperature for the second preset period of time.

Specifically, the operation may be the same as the operation of S402 shown in FIG. 4, and will not be repeatedly described herein.

In an operation of S503, the temperature of the chamber carrying the prosthetic tissue valve may be increased from the third preset temperature to the fourth preset temperature in the second increasing rate, and the prosthetic tissue valve may be incubated at the fourth preset temperature for the third preset period of time.

Specifically, a difference between the instant operation and the operation of S403 shown in FIG. 4 may be that the temperature that the chamber may eventually reach in the operation of S503 is the fourth preset temperature. In an embodiment, the operation of S403 may include: increasing the chamber carrying the prosthetic tissue valve from $-70°$ C. to $-15°$ C. in $1°$ C./min, and incubating the prosthetic tissue valve at $-15°$ C. for 1 hour.

During performing the operations of S501 to S503, the temperature of the chamber may be gradually increased to a temperature close to the critical melting temperature, decreased gradually, and then increased gradually. In such a way, crystals having slightly different sizes may further be uniformized, such that during the subsequent drying process, each area of the prosthetic tissue valve may have a same drying degree.

In addition, the operation of S103 shown in FIG. 1 may include: performing the vacuum-drying process to the prosthetic tissue valve at the fourth preset temperature at the first vacuum degree. The pressure of the first vacuum degree may be 5 Pa to 100 Pa (such as 25 Pa, 50 Pa, 75 Pa, and the like). In an embodiment, the above operation may be: performing the vacuum-drying process to the prosthetic tissue valve at $-15°$ C. and 50 Pa to completely remove free water. In other embodiments, after performing the above-mentioned first drying process, the second drying process described in the above-mentioned embodiment may be performed to further remove the water within the prosthetic tissue valve to allow the content of water in the final prosthetic tissue valve to be ≤15%. In addition, after performing the drying process, nitrogen may be filled to recover the pressure for the prosthetic tissue valve, and the prosthetic tissue valve may be sealed packaged and sterilized by ethylene oxide (EO). Sterilization by applying antioxidant and EO may avoid damages to the prosthetic tissue valve caused by other sterilization treatments and avoid oxidation of the prosthetic tissue valve when contacting oxygens during EO sterilization.

Further, the present disclosure may provide a prosthetic tissue valve, which may be manufactured by being treated by any one of the above-mentioned operations. The prosthetic tissue valve treated according to the above-mentioned embodiments may have a high biocompatibility, a rehydration property, an anticoagulant property, an anti-thrombus property, a capability of inducing endothelialization, and a long durability. The prosthetic tissue valve may be preserved in a dry state and may be flexible and exhibit high biological functions in the dry state. Costs of manufacturing and transporting the prosthetic tissue valve may be reduced, and operations of applying the prosthetic tissue valve may be simplified, providing technical support for the prosthetic tissue valve to be loaded into the delivery device immediately after being manufactured.

A method of manufacturing the prosthetic tissue valve provided by the present disclosure may further be illustrated by illustrating a specific implementation. The method of treating the prosthetic tissue valve may include following operations.

A. A prosthetic tissue valve made of bovine pericardium or porcine pericardium may be crosslinked with glutaraldehyde and washed in normal saline.

B. After the treatment of A, the prosthetic tissue valve may be placed into a first mixed solution containing EDC, NHS, and heparin, and incubated at 37° C. for 4 hours. The first mixed solution may include 3 g/L of heparin, 4 g/L of EDC, and 2.4 g/L of NHS.

C. After the treatment of B, the prosthetic tissue valve may be washed by a solution of disodium hydrogen phosphate for 2 hours, and then washed by water for injection for 24 hours.

D. After the treatment of C, the prosthetic tissue valve may be placed into a second mixed solution, incubated on a constant temperature shaker at 37° C., 100 rpm for 24 hours. The second mixed solution may include: 10% (volume fraction) of glycerin, 5% (volume fraction) of vitamin E, and 50 ng/mL of VEGF.

E. After the treatment of D, the prosthetic tissue valve may be placed into a chamber, and liquid nitrogen may be uniformly sprayed into the chamber in a mist form, such that a temperature field with scattered mist-formed liquid nitrogen may be generated to surround the prosthetic tissue valve. A concentration of the mist-formed liquid nitrogen may be adjusted to regulate a cooling rate and a degree of crystallization of the prosthetic tissue valve. Specifically, a temperature of the chamber may be decreased from an ambient temperature to 4° C. in 20° C./min; decreased from 4° C. to −15° C. in 1° C./min; and decreased from −15° C. to −70° C. in 99° C./min.

F. The temperature of the chamber may be increased from −70° C. to −15° C. in 1° C./min, and the chamber carrying the prosthetic tissue valve may be incubated at −15° C. for 1 hour. The temperature of the chamber may be decreased from −15° C. to −70° C. in 1° C./min, and the chamber carrying the prosthetic tissue valve may be incubated at −70° C. for 1 hour. The temperature of the chamber may be increased from −70° C. to −50° C. in 1° C./min, and the chamber carrying the prosthetic tissue valve may be incubated at −50° C. for 1 hour.

G. A first drying process may be performed to the chamber carrying the prosthetic tissue valve at −50° C. at 1 Pa for 4 hours. A pressure may subsequently be adjusted to be 50 Pa, and the temperature of the chamber may be increased to −15° C. to remove free water.

H. The temperature of the chamber may be increased from −15° C. to 20° C. in 0.5° C./min, and a second drying process may be performed at 1 Pa to remove a part of combined water in the prosthetic tissue valve.

A durability test is performed to the prosthetic tissue valve obtained after the treatment of H, and a failure does not occur after performing 200 million cycles of fatigue tests.

A rehydration test is performed to the prosthetic tissue valve obtained after the treatment of H, and the prosthetic tissue valve may regain fluid dynamic functions within 30 seconds after being rehydrated.

A biocompatibility test is performed to the prosthetic tissue valve obtained after the treatment of H, and test results are shown in Table 1. It may be seen from FIG. 1, the prosthetic tissue valve may have a high biocompatibility.

TABLE 1

Results of the biocompatibility test performed to the prosthetic tissue valve

| Items performed in the bio-compatibility test | Test Results |
|---|---|
| Pyrogen | Negative |
| In vitro cytotoxicity | Grade 1 |
| Delayed type hypersensitivity | Negative |
| Intracutaneous irrtation | A difference between an average value of a test group and an average value of a control group is not greater than 1.0. |
| Acute systemic toxicity | Negative |
| Sub-chronic systemic toxicity | A test group (including localized and chronic injection) does not show any toxic symptom. Histological examination shows the test group does not have significant pathological changes compared to a control group. Variations of body weights among various time points and variations of ratios of major organs to the body weights among various time points in the test group and those in the control group do not show statistical significance (P > 0.05). Each blood index in the test group and that in the control group do not show statistical significance (P > 0.05). |
| Hereditary toxicity | Ames test : mutagenicity to salmonella typhimurium is not shown. A chromosome aberration test: chromosome aberration is not shown in mammalian somatic cells. A genetic mutation test: mammals in the test group do not show genetic. |
| hemolysis | A hemolysis rate is less than 5.0%. |
| implantation test | After implanting the prosthetic tissue valve samples into muscles (1 week, 4 weeks, 12 weeks), local bioreactions in the test group and the control group do not show significant difference. |

According to the present disclosure, a temperature of the prosthetic tissue valve may be regulated to gradually decrease in a first cooling rate, which is a relative low cooling rate, such that each area of the entire prosthetic tissue valve is in a critical crystallization state uniformly. Further, the temperature of the prosthetic tissue valve may be regulated to rapidly decrease in a relatively high second cooling rate reaching a temperature lower than a crystallization temperature, such that each area of the prosthetic tissue valve may be crystallized uniformly at a same temperature, and a damage to the prosthetic tissue valve caused by the thermal stress generated by a temperature difference may be avoided. At the same time, a crystal size of each area the prosthetic tissue valve may be uniform, such that during a subsequent drying process, each area of the prosthetic tissue valve may have a same drying degree. As the temperature is regulated to rapidly decrease in the relatively high second decreasing rate, a small sized crystal may be generated, avoiding a damage to the structure of the prosthetic tissue valve caused by a large sized crystal. According to the treatment of the present disclosure, the prosthetic tissue valve may be flexible in the dry state and may have better biological functions, costs of manufacturing and transporting the prosthetic tissue valve may be reduced, and operations of applying the prosthetic tissue valve may be simplified, providing technical support for the prosthetic tissue valve to be delivered into a delivery device immediately after manufacturing.

In addition, the present disclosure may provide a feeding port on a chamber to supply liquid nitrogen in a mist form. The liquid nitrogen may be uniformly sprayed into the chamber in a mist form, such that a temperature field occupied with the mist-formed liquid nitrogen may be generated to surround the prosthetic tissue valve. The cooling rate and a degree of crystallization of the prosthetic tissue valve may be regulated by adjusting a concentration of the mist-formed liquid nitrogen within the chamber. The above-mentioned regulation may be easy, and the mist-formed liquid nitrogen serving as a medium for decreasing the temperature may have high thermal conductivity. The mist-formed liquid nitrogen may adequately contact and reduce the temperature of each area of the prosthetic tissue valve having a complex three-dimensional structure, such that each area may have a same cooling rate and a same lyophilization temperature.

In addition, according to the present disclosure, the lyophlization may be achieved through various stages of drying, residual organic solution and water in the prosthetic tissue valve may be effectively removed to improve biocompatibility.

In addition, heparin may bind to the prosthetic tissue valve via covalent bonds. In such a way, after being implanted into a patient, the prosthetic tissue valve may have an anticoagulant function and inhibit platelets from gathering. Post-surgery anticoagulant treatment may be reduced, and an incidence rate of thrombosis may be reduced. Further, a low concentration of lyoprotectant may be applied during treating the prosthetic tissue valve, reducing a damage to the prosthetic tissue valve caused by the lyoprotectant, reducing residual harmful chemical reagents, and improving biocompatibility of the prosthetic tissue valve. According to the present disclosure, antioxidant may be applied to prevent the prosthetic tissue valve from being oxidized when contacting an oxidant, increasing preservation time. A growth factor may bind to the prosthetic tissue valve via covalent bonds, such that after being implanted into the patient, a surface of the prosthetic tissue valve may be induced to be endothelialized. Endothelial cells growing on the surface of the prosthetic tissue valve may reduce post-surgery thrombus formation and reduce calcium enrichment to prevent calcification of the prosthetic tissue valve.

According to the present disclosure, treatments are performed to the prosthetic tissue valve through chemical crosslinking, enabling the prosthetic tissue valve to have the anticoagulation function and the endothelialization function after being implanted into a patient. Further, proper parameters may be applied for lyophilization of the prosthetic tissue valve, such that the prosthetic tissue valve may be preserved in a dry state without solutions. The biological tissue in the related art having poor stability and difficult to be preserved in aqueous solutions after anticoagulant and endothelialization treatments may be solved.

The above-mentioned embodiments are only embodiments of the present disclosure, and shall not limit the scope of the present disclosure. Any equivalent structural or procedure modification performed based on the specification and drawings of the present disclosure, applied directly or indirectly to other related art, shall be within the scope of the present disclosure.

What is claimed is:

1. A method of treating a prosthetic tissue valve, comprising:
   decreasing a temperature of a chamber carrying the prosthetic tissue valve from a first preset temperature to a second preset temperature in a first cooling rate, such that the prosthetic tissue valve is cooled, wherein the second preset temperature is greater than a crystallization temperature of the prosthetic tissue valve, and the second preset temperature is a critical crystallization temperature;
   decreasing the temperature of the chamber carrying the prosthetic tissue valve from the second preset temperature to a third preset temperature in a second cooling rate, such that the prosthetic tissue valve is further cooled, wherein the third preset temperature is lower than the crystallization temperature of the prosthetic tissue valve, and the second cooling rate is greater than the first cooling rate; and
   performing a drying process to the prosthetic tissue valve.

2. The method according to claim 1, wherein the prosthetic tissue valve is cooled by performing operations of:
   spraying liquid nitrogen with a mist form uniformly into an inside of the chamber carrying the prosthetic tissue valve, such that a temperature field comprising scattered mist-formed liquid nitrogen is generated to surround the prosthetic tissue valve, wherein a concentration of the mist-formed nitrogen is positively related to the cooling rate of the chamber.

3. The method according to claim 1, wherein, before the decreasing the temperature of the chamber carrying the prosthetic tissue valve from the first preset temperature to the second preset temperature in the first cooling rate, the method further comprises:
   decreasing the temperature of the chamber carrying the prosthetic tissue valve from an ambient temperature to the first preset temperature in a third cooling rate, wherein the third cooling rate is greater than the first cooling rate and smaller than or equal to the second cooling rate.

4. The method according to claim 3, wherein, before the decreasing the temperature of the chamber carrying the prosthetic tissue valve from the ambient temperature to the first preset temperature in the third cooling rate, the method further comprises:
   incubating the prosthetic tissue valve into a first mixed solution comprising a crosslinking agent and heparin to allow the heparin to covalently bind to the prosthetic tissue valve; and
   washing the heparin-bound prosthetic tissue valve.

5. The method according to claim 4, wherein
   the crosslinking agent comprises N-hydroxy succinimide (NHS) and 1-(3-Dimethylaminopropyl)-3-ethylcarbodiimide hydrochloride (EDC); and
   a concentration of the heparin in the first mixed solution is 1 g/L to 40 g/L, a concentration of NHS in the first mixed solution is 1 g/L to 10 g/L, and a concentration of EDC in the first mixed solution is 1 g/L to 50 g/L.

6. The method according to claim 4, wherein
   the first mixed solution further comprises growth factors, the growth factors comprise a vascular endothelial growth factor (VEGF), and a concentration of the VEGF in the first mixed solution is 1 ng/mL to 100 ng/mL.

7. The method according to claim 3, wherein, before the decreasing the temperature of the chamber carrying the prosthetic tissue valve from the ambient temperature to the first preset temperature in the third cooling rate, the method further comprises:
incubating the prosthetic tissue valve into a second mixed solution, wherein the second mixed solution comprises at least one of a lyoprotectant, an antioxidant, and a growth factor.

8. The method according to claim 7, wherein
the lyoprotectant comprises at least one of glycerin, trehalose, sucrose, polyvinylpyrrolidone, glycol, propylene glycol, acetamide, methanol, polyethylene glycol, and glucan;
the antioxidant comprises at least one of vitamin D, vitamin E, protein hydrolysates, sodium thiosulfate, and thiourea;
the growth factor comprise a VEGF; and
a mass fraction of the lyoprotectant and the antioxidant in the second mixed solution is not greater than 35%, and a concentration of the growth factor in the second mixed solution is 0ng/mL to 100 ng/mL.

9. The method according to claim 4, wherein when the first mixed solution or the second mixed solution does not comprise the growth factor, the method further comprises:
incubating the prosthetic tissue valve into a third mixed solution comprising the growth factor, wherein the growth factor comprises a VEGF, and a concentration of the growth factor in the third mixed solution is 1 ng/mL to 100 ng/mL.

10. The method according to claim 1, wherein, before the performing the drying process to the prosthetic tissue valve, the method further comprises:
increasing a temperature of a chamber carrying the prosthetic tissue valve from a third preset temperature to a fourth preset temperature in a first increasing rate, incubating the chamber carrying the prosthetic tissue valve at the fourth preset temperature for a first preset period of time, wherein the fourth preset temperature is lower than a melting point of the prosthetic tissue valve, and the fourth preset temperature is a critical melting temperature;
decreasing the temperature of the chamber carrying the prosthetic tissue valve from the fourth preset temperature to the third preset temperature in a fourth cooling rate, incubating the chamber carrying the prosthetic tissue valve at the third preset temperature for a second preset period of time; and
increasing the temperature of the chamber carrying the prosthetic tissue valve from the third preset temperature to a fifth preset temperature in a second increasing rate, incubating the chamber carrying the prosthetic tissue valve at the fifth preset temperature for a third preset period of time, wherein the fifth preset temperature is lower than the fourth preset temperature.

11. The method according to claim 10, wherein the performing the drying process to the prosthetic tissue valve comprises:
performing a first vacuum-drying process to the prosthetic tissue valve at the fifth preset temperature at a first vacuum degree for a fourth preset period of time; and
performing a second vacuum-drying process to the prosthetic tissue valve at the fourth preset temperature at a second vacuum degree to completely remove free water in the prosthetic tissue valve, wherein the second vacuum degree is less than the first vacuum degree.

12. The method according to claim 11, wherein, after the performing the second vacuum-drying process to the prosthetic tissue valve at the fourth preset temperature at a second vacuum degree to completely remove free water in the prosthetic tissue valve, the method further comprises:
increasing the temperature of the chamber carrying the prosthetic tissue valve from the fourth preset temperature to a sixth preset temperature in a third increasing rate; and
performing a third vacuum-drying process to the prosthetic tissue valve at the sixth preset temperature at a third vacuum degree, wherein the second vacuum degree is less than the third vacuum degree.

* * * * *